(12) United States Patent
Pavlakos

(10) Patent No.: US 6,882,732 B2
(45) Date of Patent: Apr. 19, 2005

(54) INTERNET-BASED AUDIOMETRIC TESTING SYSTEM

(76) Inventor: Chris M. Pavlakos, 511 W. Whipp Rd., Dayton, OH (US) 45459

( * ) Notice: Subject to any disclaimer, the term of this patent is extended or adjusted under 35 U.S.C. 154(b) by 831 days.

(21) Appl. No.: 09/737,243

(22) Filed: Dec. 14, 2000

(65) Prior Publication Data

US 2002/0076056 A1 Jun. 20, 2002

(51) Int. Cl.[7] ............................................... H04R 29/00
(52) U.S. Cl. ............................ 381/60; 381/58; 600/559
(58) Field of Search ...................... 381/58, 60; 600/559; 73/585

(56) References Cited

U.S. PATENT DOCUMENTS 3,906,158 A * 9/1975 Lake ............................. 73/585
6,522,988 B1 * 2/2003 Hou ............................ 702/122

OTHER PUBLICATIONS

Sarel et al. ; A system and method . . . self testing . . . of subjects; Jan. 22, 1998, WO 98/02083.*

* cited by examiner

Primary Examiner—Melur Ramakrishnaiah
(74) Attorney, Agent, or Firm—R. William Graham

(57) ABSTRACT

A test site Internet-based client CPU has hearing testing equipment operably connected therewith to produce tones in a first test to which a test person responds in a manner utilized by the test site Internet-based client CPU and which produces a first test data signal corresponding to the response. Software is preferably operably provided in the system for manipulating the first test data signal to produce a first output data indicative of one characteristic of said test person's hearing level. Further, a remote Internet-based server CPU is provided which preferably includes software for gathering the first output data and personal information data of the person and presenting the data in a predetermined audiological test report data form for review by a person certified in audiometric testing.

10 Claims, 11 Drawing Sheets

FIG. 2

Audi5

File  Company  Employee

Current Company: APOGEE INC.    Employee:

HINT: Select a Company or add a new one. Then Press the NEXT Button.

| Company | Employees | History | Test | Results | Reports |

Select a Company: Apogee, Inc.

Company   APOGEE INC.
Address 1 313 NARROWS TRACE
Address 2 SUITE #100
City      BEAVERCREEK    State OH  Zip 45385    Additional Information Do NOT Use Age Correction Factors ☐

Contacts

Primary
Name
  First  Dimitri
  Last   Preonas
Phone    937-320-1530

Emergency
Name
  First  Steve
  Last   Stephenson
Phone    937-320-1535

Add A New Company

➡ NEXT

Audi5
File  Company  Employee

Current Company: APOGEE INC.    Employee: STEPHENSON, STEPHEN

HINT: Fill in/change the answers/check boxes and press the NEXT button.

| Company | Employees | History | Test | Results | Reports |

History as of . 9/21/00

Old History:

|  | R | L | No |
|---|---|---|---|
| Ringing in your ears | ✓ |  |  |
| Ear Operation |  |  | ✓ |
| Punctured Ear Drum |  |  | ✓ |
| Draining from your ears |  |  | ✓ |
| Earaches |  | ✓ |  |

Exposed to noises such as...
- Snowmobiles ✓
- Gunfire ✓
- Motorcycles ✓
- Rock Music
- Farm Equipment ✓
- Other ✓

Explain: POWER TOOLS

|  | Yes | No |
|---|---|---|
| Dizziness |  | ● |
| Head Injuries | ● |  |
| Family Hearing Loss |  | ● |
| Allergies/Hayfever | ● |  |
| Rx/OTC Meds | ● |  |
| Quiet Rule | ● |  |
| Upper Respitory Inf/Sinus |  | ● |
| Training | ● |  |
| Trouble Hearing |  | ● |
| Military Service | ● |  | Air Force |
| Exposed to gunfire or loud noises while in the service? | ● |  |

→ NEXT

Audi5

File  Company  Employee

Current Company: APOGEE INC.  Employee: STEPHENSON, STEPHEN

HINT: Press Start Test, then Fill in all Fields and press Next Calculate Results.

| Company | Employees | History | Test | Results | Reports |

Testing   Start Test   Date:   Time:

Audi5

File  Company  Employee

Current Company: APOGEE INC.    Employee: STEPHENSON, STEPHEN

HINT: Run a report. Then Click back on 'Next Employee' to continue.

| Company | Employees | History | Test | Results | Reports |

Reports

Print to:  ○ Screen  ○ Printer
Report Dates: From: 9/21/00  To: 9/21/00

Employee:
- Current Employee Hearing Evaluation Report
- All - Employee Hearing Evaluations Company:
- Audiometric Summary Report
- Audiometric Test Report
- Audiometric Classification Report (Baseline)
- Audiometric Classification Report (Annual)
- Employee Hearing Protection Report All Reports Next Employee    Exit

INTERNET-BASED AUDIOMETRIC TESTING SYSTEM

BACKGROUND OF THE INVENTION

1. Field of the Invention

The invention relates to audiometric testing systems. More particularly, the invention relates to an Internet-based audiometric system.

2. Description of the Prior Art

Many companies are required to comply with annual hearing tests for employees to check for problems relating to the harmful effects of job-related noise. Such companies are subject to liability for hearing damage which can be shown to have been caused by the noisy environment of the company. Consequently, the company typically employs an independent audiologist to conduct such tests and provide the report whether hearing threshold shifts have occurred and for what reasons they may have occurred.

Audiometric testing techniques are well known. Some known audiometric testing techniques are described in "Audiometry: Principles and Practices", by Aaron Glorig, M.D., Williams & Wilkons Co., Baltimore, Md., 1965. Threshold bracketing techniques are utilized to determine a person's hearing thresholds at various frequencies by incrementing or decrementing the intensity of a test tone applied to one of the subject's ears until he or she satisfactorily indicates that he or she has heard the test tone. A quantity known as the "pure tone average" is commonly computed by averaging the subject's threshold at three frequencies, such as 500, 1,000, and 2,000 cycles per second. Also, percent binaural impairment indicates deviation from average or standard hearing levels.

There exist audiometric test systems and methods for testing one's hearing to determine threshold levels at various frequencies, automatically computing audiometric parameters from such threshold levels, automatically determining the presence of any significant threshold level shifts of the subject by comparing the subject's present test results with the prior test results, and automatically indicating the presence of any significant threshold level shifts.

While various audiometers are known, including manual audiometers and automatic audiometers, none of the current systems provide for suitably tracking a transient employee and hearing history. Also, none of the existing systems easily account for audiology in view of protective aids worn in the environment. The present invention overcomes these problems.

BRIEF SUMMARY OF THE INVENTION

It is an object of the invention to improve audiology.

It is another object to reduce risk to companies required to provide audiological testing for employees by providing the present invention.

It is another object to track transient employees through an Internet-based audiological testing system.

It a further object to provide an improved audiological testing system for use by those certified to test in the field of audiology.

Accordingly, the present invention is directed to an Internet-based audiometric testing system. The system includes a test site Internet-based client CPU having hearing testing equipment operably connected therewith to produce tones in a first test to which a test person responds in a manner utilized by the test site Internet-based client CPU and produces a first test data signal corresponding to the response. Software is preferably operably provided in the system for manipulating the first test data signal to produce a first output data indicative of one characteristic of said test person's hearing level. Further, a remote Internet-based server CPU is provided which preferably includes software for gathering the first output data and personal information data of the person and presenting the data in a predetermined audiological test report data form for review by a person certified in audiometric testing.

A CPU located at the certified person site is provided for receiving the test report data form to enable review thereof. The CPU at the certified person's site equipped with software for transmitting the report data form to the test site Internet-based client CPU via the remote server CPU along with verified signature of one of acceptable and non-acceptable level of hearing for the test subject to the test site Internet-based client CPU.

Other objects and advantages will be readily apparent to those skilled in the art upon viewing the drawings and reading the detailed description hereafter.

BRIEF DESCRIPTION OF THE DRAWINGS

FIG. 2 depicts a screen view of the present invention.

Figure 3:
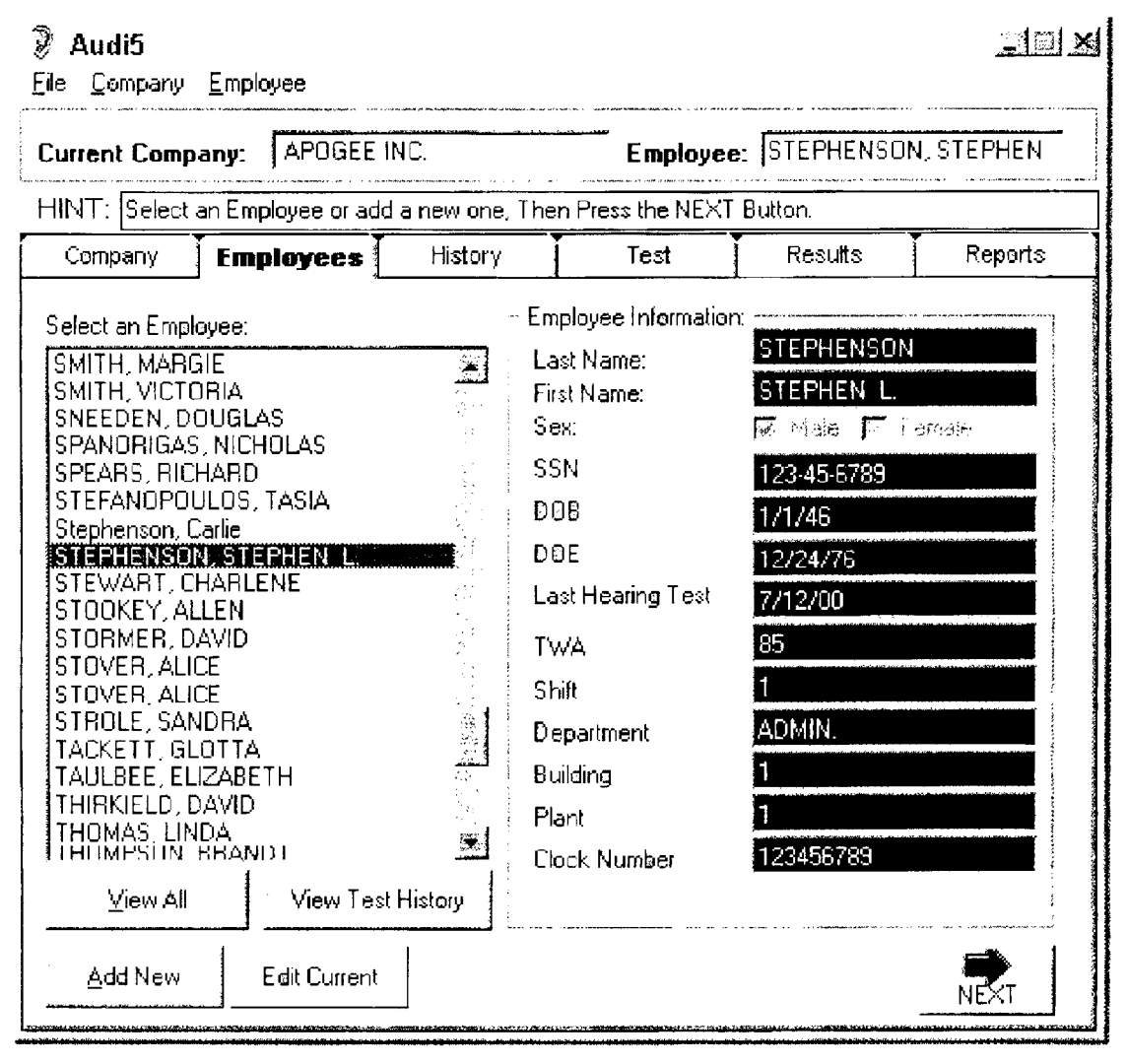

FIG. 3 depicts another screen view of the present invention.

FIG. 4a depicts still another screen view of the present invention.

FIG. 4b depicts yet another screen view of the present invention.

FIG. 5a depicts another screen view of the present invention.

FIG. 6a depicts another screen view of the present invention.

FIG. 7 depicts yet another screen view of the present invention.

DETAILED DESCRIPTION OF THE INVENTION

Figure 1:
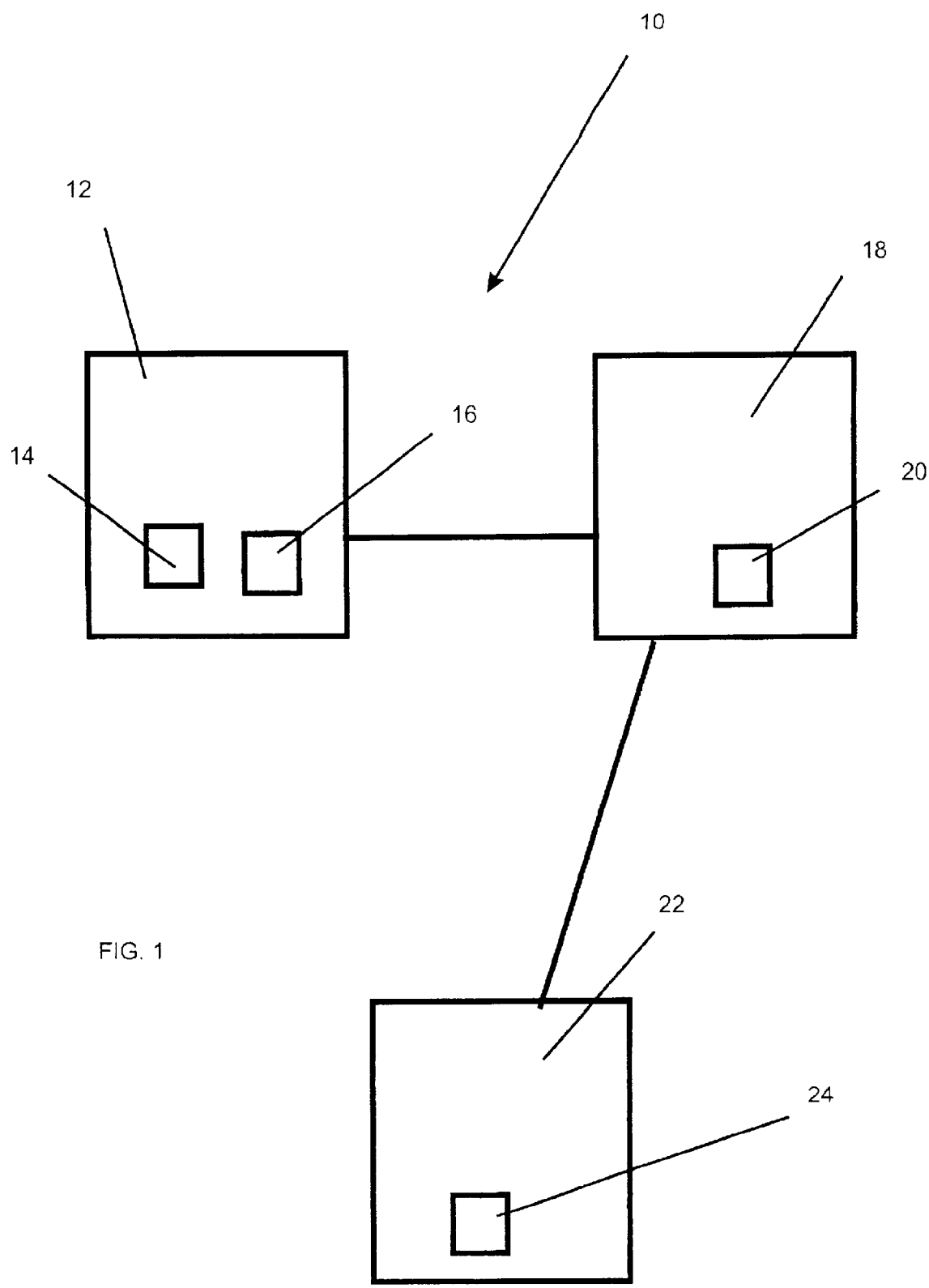
FIG. 1 is a schematic diagram of the present invention.

Referring now to the drawings, the Internet-based audiometric testing system of the present invention is generally referred to by the numeral 10. The system includes a test site Internet-based client CPU 12 having hearing testing equipment 14 operably connected thereto in a manner to produce tones in a first test to which an employee of a company, for example, responds via a keyboard, touch screen, or other signal producing response device, which is done at the company site. Audiometric software 16 shown here on the CPU 12 receives the responsive signal which enables producing a first test data signal corresponding to the response, but could be located on the Internet-based CPU 18, for example. Audiometric software 16 is provided for manipulating the first test data signal to produce a first output data indicative of one hearing characteristic of the test person's hearing level. The audiometric software 16 can reside on the CPU 12 to work in conjunction with the hearing testing equipment 14. By way of example, audiometric test tones can be produced by programmable analog circuitry including programmable oscillators for determining test tone frequencies and programmable attenuators responsive to signals produced by the programmable oscillators.

A remote Internet-based server CPU 18 is also provided and has audiometric software 20 for receiving the first output data and personal information data of the employee and presenting the data in a predetermined audiological test report data form for review by a person certified in audiometric testing. Accordingly, it is preferable that the software 16 and 20 be web-based and reside on the remote Internet-based server CPU 18 and remains accessible via the Internet. In this regard, the invention provides an application service provider aspect.

An Internet-based CPU 22 located at the certified person's site is provided for receiving the test report data form to enable review thereof. Preferably also residing on the remote Internet-based server CPU 18 (which can reside on CPU 22) is software 24 to enable transmission of the report data form to the test site Internet-based client CPU 12 preferably via the remote server CPU 18 along with a verified signature of one of acceptable and non-acceptable level of hearing for the employee. In addition, other recommendation information can be transmitted in the report form.

It is understood that the Internet-based audiometric testing system 10 can produce/receive a series of tones in a series of tests in a manner as described to generate a series of output data signals, each indicative of a distinct characteristic of the employee's hearing level. The software 20 obtains the series of output data signals and associates them with the personal information data of the employee to be used in the predetermined audiological test report data form. The report data form includes diagnostic information, including information confirming a threshold level shift detected at a testing session, hearing loss, hearing protection needed, and/or recommending subsequent audiometric testing dates, referral and/or treatment.

Preferably, the remote Internet-based server CPU 18 stores in memory resident thereon the output data for the employee along with the personal information data. The software 20 preferably includes means for automatically editing the personal information data and output data upon subsequently receiving of the data to create a historical database of the employee. Each of the personal information data and test output data are preferably stored in a record file in memory of the CPU 18. It is also contemplated that the software 20 includes an operating algorithm and a random access memory for storing audiometric records for all employees, for example, of a company and as well as a plurality of companies, each having employees.

The software 16 includes means for comparing the subsequent output data to a prior output data to produce a comparison output data indicative of whether a predetermined percentage variation is exceeded. The report data form includes all output data and the comparison output data. Via the CPUs 12 and 18, the software 16 enables entry of environmental noise input data which is utilized said noise in producing the test output data. Further, the CPUs 12 and 18, software 16 enable entry of noise reduction rating for equipment utilized by the employee which is utilized in producing test output data. Preferably, the software 16 also provides for the entry of personal information data, such as name, address, telephone number, age, sex, date of birth, social security number. In order to provide the fullest scope application of the Internet-based invention 10, the personal information data includes a unique identifier which identifies the employee, which can be the social security number, for example. This provides the unique advantage of enabling a more positive tracking mechanism of the employee's hearing test results and can be shared by all employers regardless of the employee's mobility.

More particularly, FIGS. 2–11 present a screen by screen view of what a person would see at each phase of operation of the invention as enabled by the software 16, 20, and 24. While the software 16, 20 and 22 are described as separate components, it is understood that it is the functional features which are so described and may be collectively operably associated together as shown in FIG. 1.

Figure 4B:
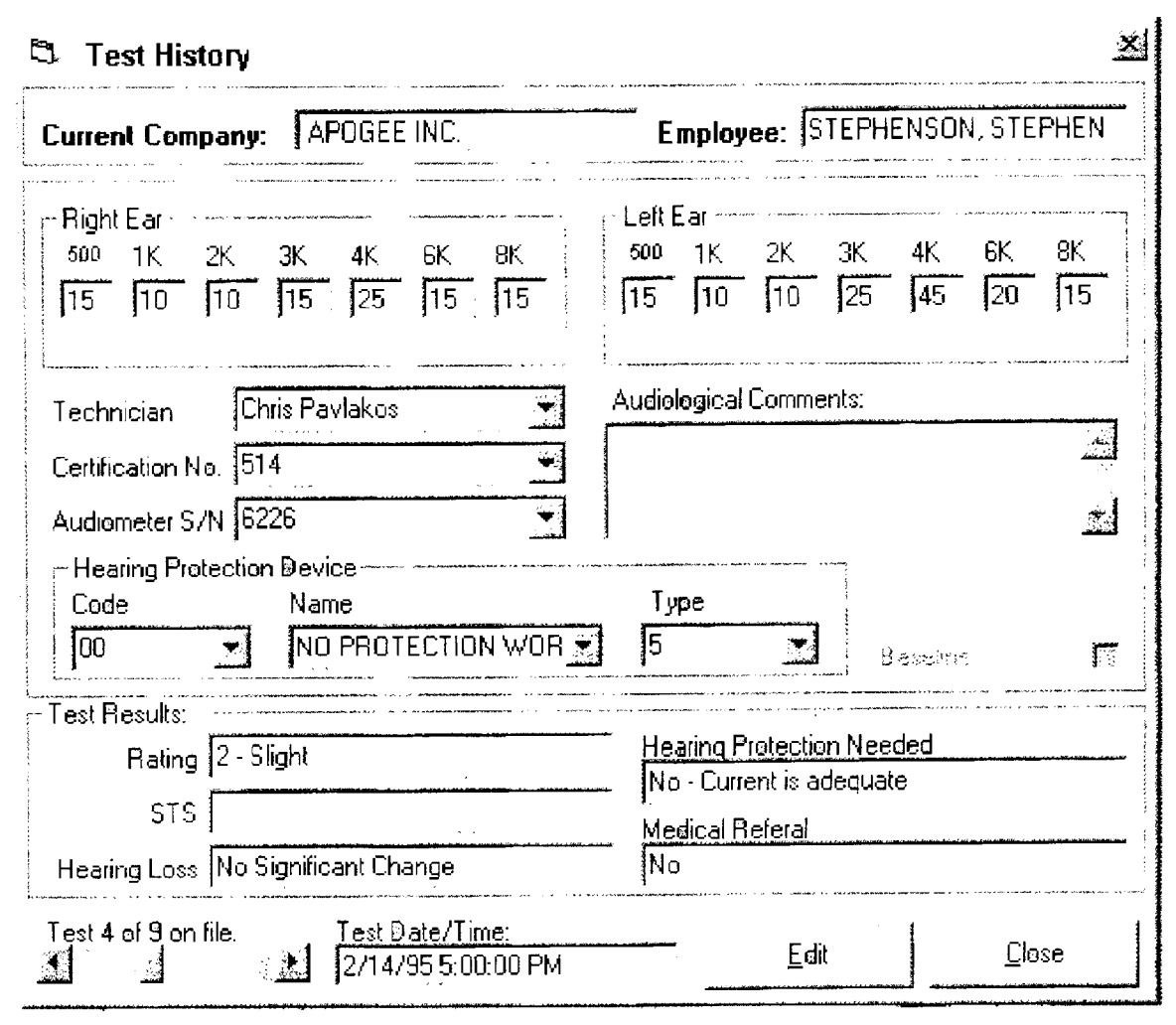

The Internet-based system enables one to select/add a company as seen in the Company tab of FIG. 2. The Employees tab FIG. 3 permits display of an employee list, with a particular employee selected shown here. FIG. 4a enables selection of the History tab which shows the history of the employee and enables addition/editing of data concerning the employee. For example, ringing in ears, ear operation, punctured drum, ear drainage, earaches, variety of environmental noise exposure, snowmobile, gunfire, motorcycle, rock music, farm equipment, etc, and enable entry of indication of dizziness, head injury, family hearing loss, allergies, prescriptions, quiet rule, upper respiratory/ sinus problem, training, trouble hearing, military service and type of noise exposure. FIG. 4b further expounds on the test history of the patient and is accessed through by selecting a Next button shown in FIG. 4a.

Figure 5B:
FIG. 5b depicts yet another screen view of the present invention.
Figure 5C:
FIG. 5c depicts still another screen view of the present invention.
Figure 6A:
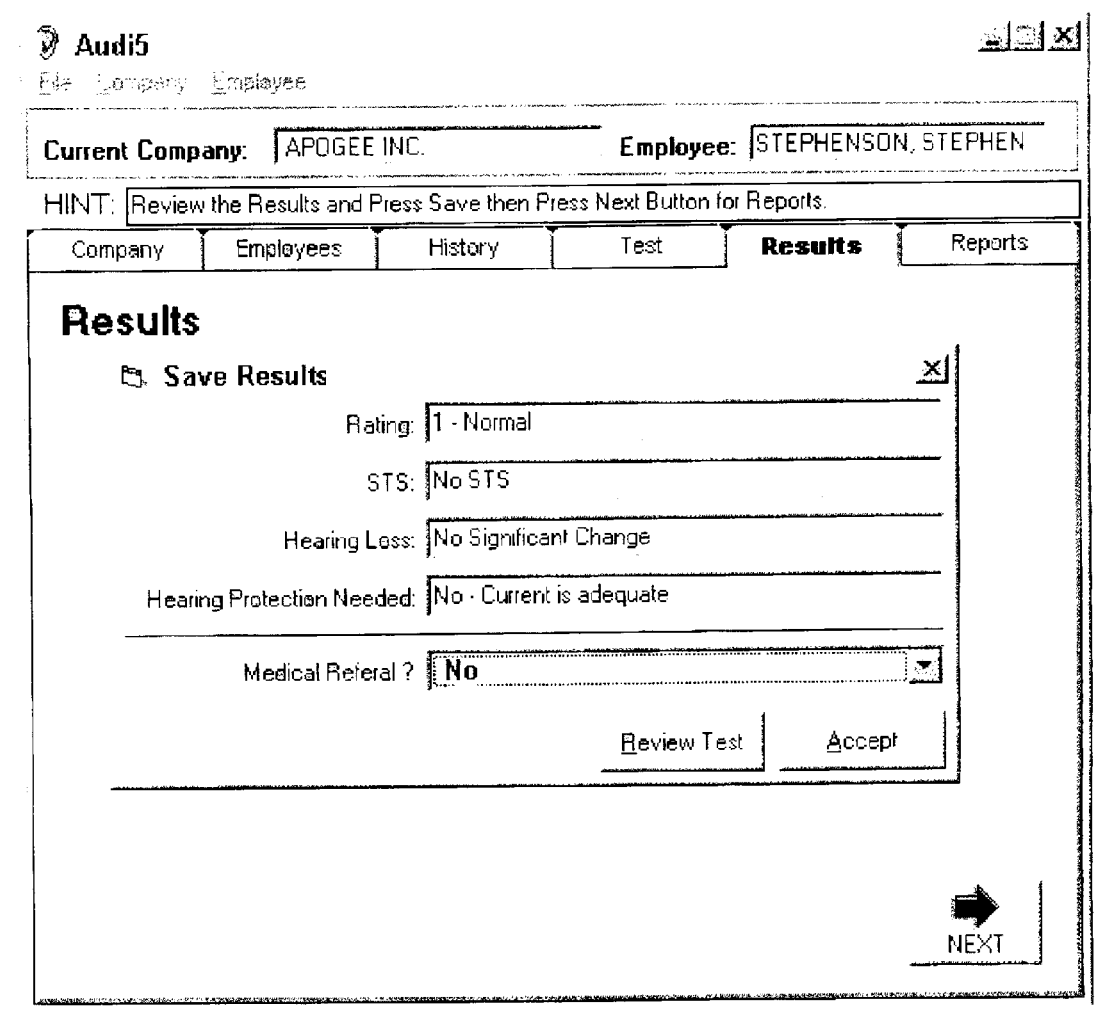
Figure 6B:
FIG. 6b depicts still another screen view of the present invention.

The Test tab in FIG. 5a enables one to conduct a new hearing test using the equipment previously described. Selecting the "Start Test" button brings up the screen shown in FIG. 5b wherein the fields therein are blank prior to testing. FIG. 5c depicts the same testing screen with subsequent to testing with the test fields filled. FIG. 6a depicts the Results tab wherein the present invention takes hearing test results of the right and left ear with environmental noise and ear protection device to be worn and the noise reduction rating thereof gathered in FIG. 5 and utilizes an algorithm within software 20 to compares the current test results with those from its historical database to determine whether there is a significant change, whether different hearing protection is required, or a medical referral is required. An option is provided to either review or accept the results whereupon accepting results (FIG. 6b) places the results in the historical database for the employee. A Reports tab in FIG. 7 enables the user to print out a variety of reports relating to the audiometric test results as shown therein.

It is noted that certain screens, such as FIGS. 6a, 6b, and 7 are designed to be edit accessible by the audiometric technician. The software 24 and 20 are designed with security access in this regard and provide signature verification from the technician to patient.

The above described embodiments is set forth by way of example and is not for the purpose of limiting the present invention. It will be readily apparent to those skilled in the art that obvious modifications, derivations and variations can be made to the embodiment without departing from the scope of the invention. Accordingly, the claims appended hereto should be read in their full scope including any such modifications, derivations and variations.

What is claimed is:

1. An Internet-based audiometric testing system, which includes:

a test site Internet-based client CPU having hearing testing equipment operably connected therewith to produce tones in a first test to which a test person responds in a manner such that audiometric software means operably associated with said test site CPU utilizes said response for producing a first test data signal corresponding to said response, said software means is further characterized to manipulate said first test data signal to produce a first output data indicative of one characteristic of said test person's hearing level;

a remote Internet-based server CPU having means for receiving said first output data and personal information data of said person and presenting said data in a predetermined audiological test report data form for review by a person certified in audiometric testing;

a CPU located at said certified person site for receiving said test report data form to enable review thereof, said CPU at said certified person's site equipped with means for transmitting said report data form to said test site Internet-based client CPU via said remote server CPU along with verified signature of one of acceptable and non-acceptable level of hearing for said test subject to said test site Internet-based client CPU.

2. The Internet-based audiometric testing system of claim 1, wherein tones in a second test are produced to which said test person responds in a manner utilized by said software means for producing a second test data signal corresponding to said response, said manipulating means manipulates said second test data signal to produce a second output data signal indicative of another characteristic of said test person's hearing level and said receiving means further receives said second output data signal and associated with said personal information data of said person and presents said data in said predetermined audiological test report data form.

3. The Internet-based audiometric testing system of claim 2, wherein said remote Internet-based server CPU includes means for editing said personal information data and output data upon subsequent receiving of said data to create a historical database of said test person.

4. The Internet-based audiometric testing system of claim 2, wherein said manipulating means further compares said second output data to said first output data to produce a comparison data whether a predetermined, percentage variation is exceeded and wherein said report data form includes all said output data and said comparison output data.

5. The Internet-based audiometric testing system of claim 1, wherein said remote Internet-based server CPU stores said output data for said test person along with said personal information data.

6. The Internet-based audiometric testing system of claim 1, wherein said test site Internet-based client CPU permits entry of environmental noise input data and wherein said software means utilizes said noise in producing said first output data.

7. The Internet-based audiometric testing system of claim 1, wherein said test site Internet-based client CPU permits entry of noise reduction rating for equipment utilized by the person and wherein said software means utilizes said noise reduction rating for equipment in producing said first output data.

8. The Internet-based audiometric testing system of claim 1, wherein said software means resides on one of said test site Internet-based client CPU and said remote Internet-based server CPU.

9. The Internet-based audiometric testing system of claim 1, wherein said software means resides on one of said test site Internet-based client CPU, said remote Internet-based server CPU, and CPU located at said certified person site.

10. The Internet-based audiometric testing system of claim 1, wherein said personal information data includes a unique identifier.

* * * * *